United States Patent
Mezzoli (10) Patent No.: US 7,063,686 B2
(45) Date of Patent: Jun. 20, 2006

(54) NOZZLE FOR ADMINISTRATIONS AND LAVAGES OF NASAL CAVITIES AND SIMILAR

(76) Inventor: Giorgio Mezzoli, Via Ricci Curbastro, 56/1-48022, Lugo (IT)

( * ) Notice: Subject to any disclaimer, the term of this patent is extended or adjusted under 35 U.S.C. 154(b) by 67 days.

(21) Appl. No.: 10/343,069

(22) PCT Filed: Jul. 23, 2001

(86) PCT No.: PCT/EP01/08483

§ 371 (c)(1),
(2), (4) Date: Jan. 24, 2003

(87) PCT Pub. No.: WO02/07894

PCT Pub. Date: Jan. 31, 2002

(65) Prior Publication Data

US 2003/0158527 A1    Aug. 21, 2003

(30) Foreign Application Priority Data

Jul. 26, 2000    (IT) ............................. MI2000A1713

(51) Int. Cl.
*A61M 31/00*    (2006.01)

(52) U.S. Cl. ..................... 604/275; 239/461; 239/469; 239/470; 239/483; 222/566; 128/200.18; 128/200.14

(58) Field of Classification Search ............ 604/68–72, 604/43, 39, 239, 257–262, 264, 275, 279, 604/295, 912; 239/461, 463, 469, 470, 483; 222/74, 320, 330, 378, 379, 322, 566, 565, 222/575, 570; 128/200.18; 606/108, 109

See application file for complete search history.

(56) References Cited

U.S. PATENT DOCUMENTS

| | | | |
|---|---|---|---|
| 2,141,077 A | | 12/1938 | Baker |
| 3,062,456 A | | 11/1962 | Thompson et al. |
| 5,046,877 A | * | 9/1991 | Longo .................. 401/266 |
| 5,067,655 A | * | 11/1991 | Farago et al. ............ 239/124 |
| 5,533,501 A | * | 7/1996 | Denyer ................ 128/200.21 |
| 5,685,869 A | * | 11/1997 | Py ...................... 604/294 |
| 6,228,070 B1 | * | 5/2001 | Mezzoli .................. 604/257 |
| 6,354,519 B1 | * | 3/2002 | Kidooka et al. .......... 239/491 |
| 6,394,366 B1 | * | 5/2002 | Adams .................. 239/463 |
| 6,478,196 B1 | * | 11/2002 | Fuchs .................. 222/321.6 |

FOREIGN PATENT DOCUMENTS

| | | |
|---|---|---|
| DE | 960 777 C | 3/1957 |
| WO | WO 96/29044 A | 9/1996 |

* cited by examiner

*Primary Examiner*—Cris Rodriguez
(74) *Attorney, Agent, or Firm*—Abelman, Frayne & Schwab (57) ABSTRACT

A nozzle having an ejection duct structured so as to allow a better distribution of the substances on the inner panes of nasal cavities and similar, such as auricular, vaginal and rectal cavities is described. A conical central portion is mounted in the nozzle outlet portion with its base in the outlet opening providing an annular fluid outlet, the conical central portion is rigidly secured to the inner wall of the outlet portion with baffles. In different embodiments of the invention the outlet portion, the central portion, the baffles and the annular outlet opening vary in shape.

22 Claims, 7 Drawing Sheets

Fig. 1

PRIOR ART

NOZZLE FOR ADMINISTRATIONS AND LAVAGES OF NASAL CAVITIES AND SIMILAR

FIELD OF THE INVENTION

The present invention relates to a nozzle able to diffusely distribute substances on the inner paries of nasal cavities and similar.

PRIOR ART

Considering for example the nasal cavities, the mucosa is a tissue having a very high absorption level owing to its extensive vascularization making it a pharmaceutical administration route able to give systemic effects. The substances administered by nasal route are in spray or drops form, the latter being preferred as they are able to cover a wider nasal surface and therefore a greater absorption area. On the other hand, in order to achieve this desirable covering, the patient must receive the administration in supine position with his head backwards reclined, and then moving his head from right to left (Remington's Pharmaceutical Sciences, 18th ed., p. 1526).

The same need is felt to reach the nasal surface as large as possible is also found in the nasal lavages useful for the removal of the secretions which may generate respiratory difficulties, inflammations of the mucosa and however which may compromise the correct functionality of the organ.

The nasal applicator nozzles present on the market have openings taking to the distribution of lavage and/or pharmacological solutions nearly exclusively along the central axis of the nasal cavity and thereby they do not allow an adequate spraying of the inner walls of the nasal cavity.

This results in incomplete lavages, as any secretion adherent to the mucosa covering the walls of the nasal cavity is removed with difficulty, and/or in an inadequate distribution of the active principles on the surface of the nasal mucosas for the absorption.

Therefore the need is felt to develop new nasal applicator nozzles allowing the uniform distribution of solutions in the whole nasal cavity.

Figure 1:
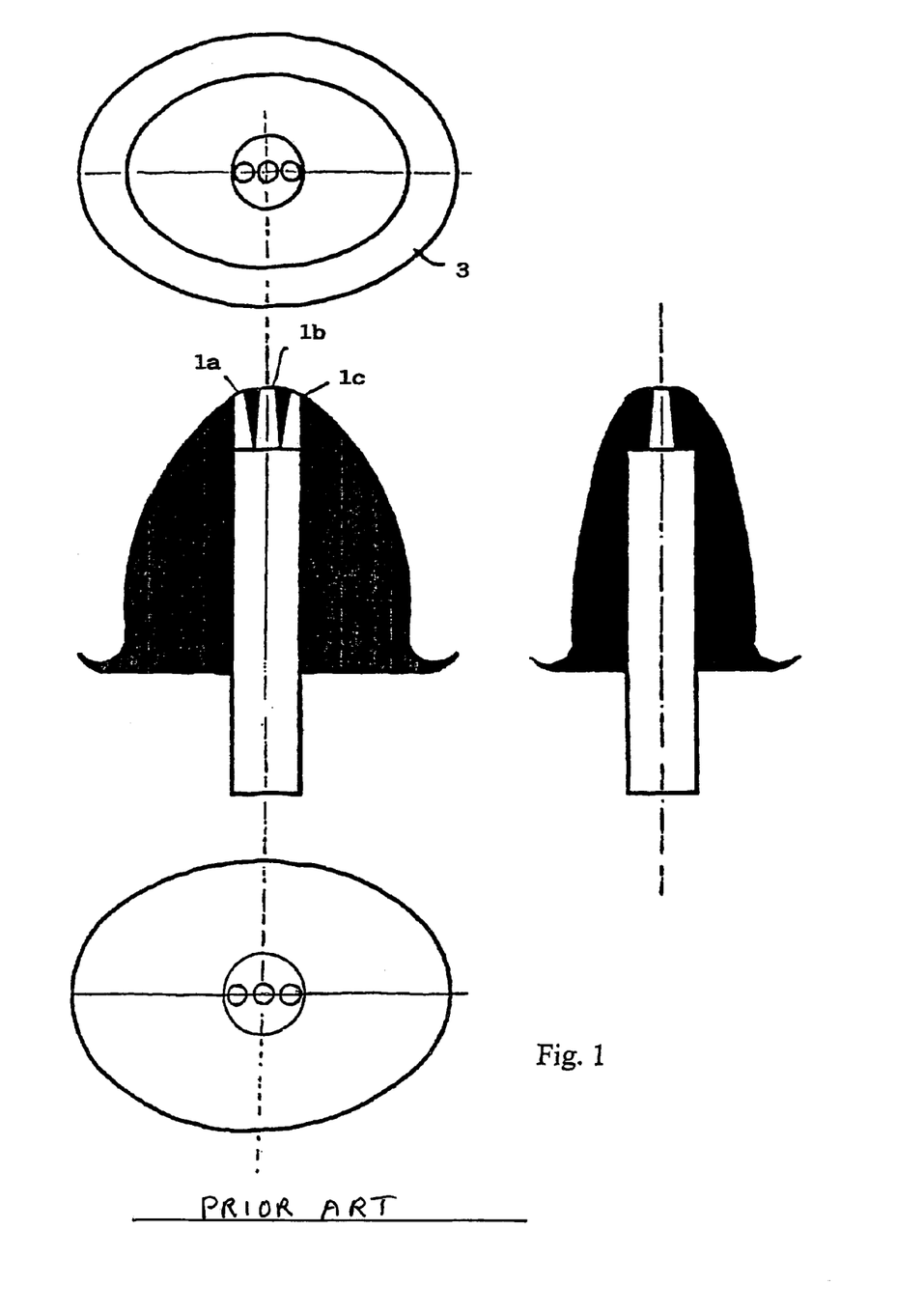
in FIG. 1 a section of the nozzle of the Patent Application WO 96/29044 is represented.

A solution to the above mentioned problem has been described in the Patent Application WO 96/29044 (to Mezzoli) which discloses a nasal irrigation device. In a preferred application of this invention, the nozzle of the device has three little channels with three outlet holes (1a), (1b) and (1c), as illustrated in FIG. 1, slightly divergent with respect to the major symmetry plane of the nozzle, in order to effectively direct the jets towards the three meata of the nasal cavities. Now we have surprisingly found a new kind of nozzle having openings of form such as to allow an even better distribution of the substances on the inner paries, of the nasal cavities and similar.

SUMMARY OF THE INVENTION

The present invention refers to a nozzle for introducing substances into the nasal cavities and similar, such as auricular, vaginal and rectal cavities, characterized in that it comprises a cylindrical ejection duct coaxial with the nozzle, having a preferably circular or elliptical section, at least a slot opening (2), preferably (semi)circular or (semi)elliptical, and a cone shaped central body (1) coaxial with the nozzle, preferably having elliptical or circular section, having the basis at the opening (2) and the vertex directed towards the basis of the nozzle and at least a baffle (3) connecting the central body (1) to the internal walls of the ejection duct.

BRIEF DESCRIPTION OF THE FIGURES

The invention will be described with reference to examples of embodiments having not limitative character, illustrated in the appended Figures wherein.

The FIGS. 2a and 2b show, respectively, a top view and a section corresponding to the base plane of a nozzle of the present invention.

The FIG. 3 shows a longitudinal section of a nozzle according to the present invention.

The FIG. 4 shows a transparent view of the ejection duct of the nozzle according to the present invention.

The FIG. 5 shows a transparent view of another embodiment form of the ejection duct of the nozzle according to the present invention, having only one aperture (2).

The FIG. 6 shows a further embodiment form of the ejection duct of the partially sectioned nozzle, having a spiral shaped baffle around the central axis.

In the appended Figures the corresponding elements will be identified by the same numerical references.

DETAILED DESCRIPTION

The nozzle of the present invention is characterized in that it includes a cylindrical ejection duct, having a preferably elliptical or circular section, coaxial with the nozzle, al least a substantially annular slot opening (2), a central body (1), having the shape of a cone with preferably elliptical or circular section coaxial with the nozzle, having the basis at the opening (2) and the vertex directed towards the basis of the nozzle, and at least a baffle (3) connecting the central body (1) to the internal walls of the ejection duct.

The nozzle of the invention may have any form suitable to the applicative needs. Preferably it has an elliptical section in order to better fit the conformation of the nostrils, and as such it is described by the Figures of the present text, but only for exemplification. By elliptical section we mean a section having a major (a) symmetry axis and a minor (b) symmetry axis where (a) is different from (b).

The opening (2) has a preferably elliptical or circular shape.

Figure 3:
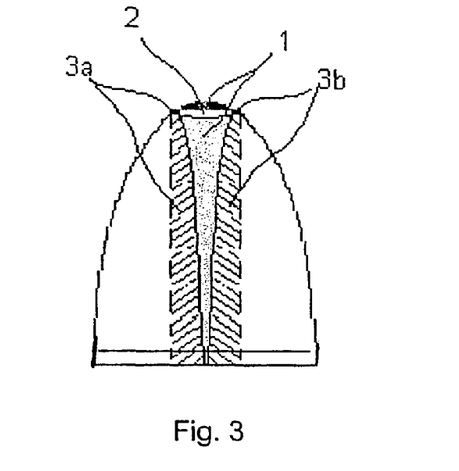
Figure 4:
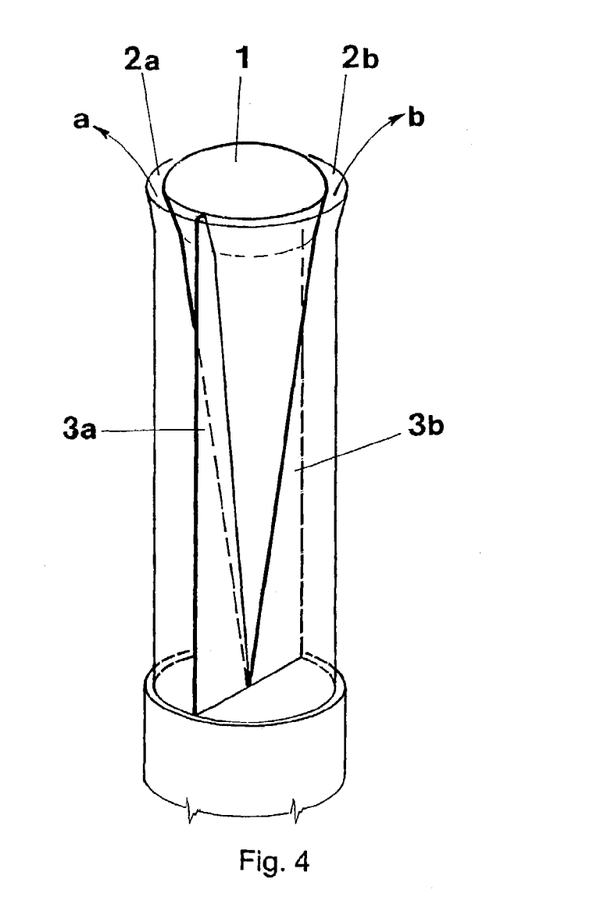

According to particularly preferred embodiments, the nozzle of the present invention has only one baffle (3) (FIG. 6), usually spiraling around the central body, or two baffles (3a) and (3b) (FIGS. 3 and 4).

The at least one baffle may reach as far as the whole height of the body or may be only at the lower or upper portion of the ejection duct.

The two baffles (3a) and (3b) moreover may be reduced to two short segments at any portion of the ejection duct.

The two baffles (3a) and (3b) are preferably aligned one to the other and, in the zone where they are present, they divide the ejection duct in two zones (2a) and (2b), having semielliptical or semicircular section and decreasing extent from bottom to top.

In the case the baffles (3a) and (3b) reach the opening (2) they divide it in two openings (2a) and (2b) having semielliptical or semicircular section.

In the case the baffle (3) is spiral shaped it may be free to rotate around the central body (1).

Figure 2A:
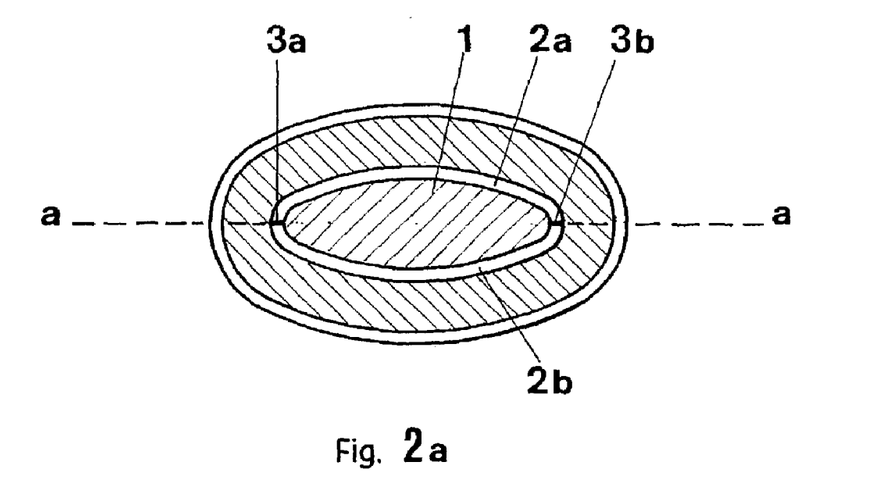

The FIG. 2a represents a top view of the nozzle according to the present invention, having two baffles (3a) and (3b) connecting the solid central body (1) to the internal walls of the ejection duct, said baffles dividing the opening (2) in two openings (2a) and (2b) having semielliptical or semicircular shape.

Figure 2B:
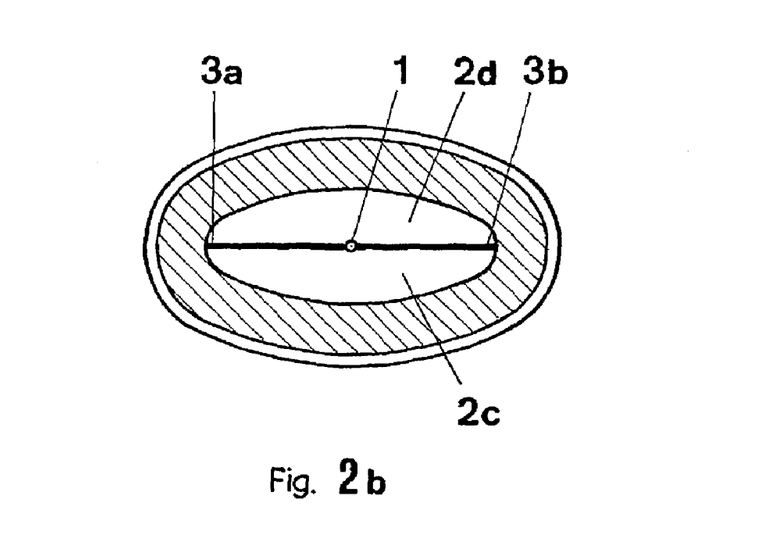

The FIG. 2b represents a section of the same nozzle at the basis plane, wherein (1) is the solid central body, (3a) and (3b) are the two baffles which connect it to the walls of the ejection duct and (2c) and (2d) are the two zones wherein the ejection duct is divided by said baffles.

The FIG. 3 discloses a longitudinal section of the nozzle of the invention along the (a—a) line of FIG. 2a. The central body (1) is connected to the walls of the ejection duct, described by the dashed lines, by the baffles (3a) and (3b).

The FIG. 4 shows a transparent view of the ejection duct of the nozzle of the invention. The particular conformation of the body (1), connected to the internal walls of the ejection duct by the baffles (3a) and (3b), and of the ejection duct, having the upper end of the side wall widened towards the outside, carries the liquid from the tube to come out according to the direction of the arrows (a) and (b). The nozzle of the present invention then allows to direct the flux in an extremely diffused manner on the internal walls of the nasal mucosa.

Figure 5:
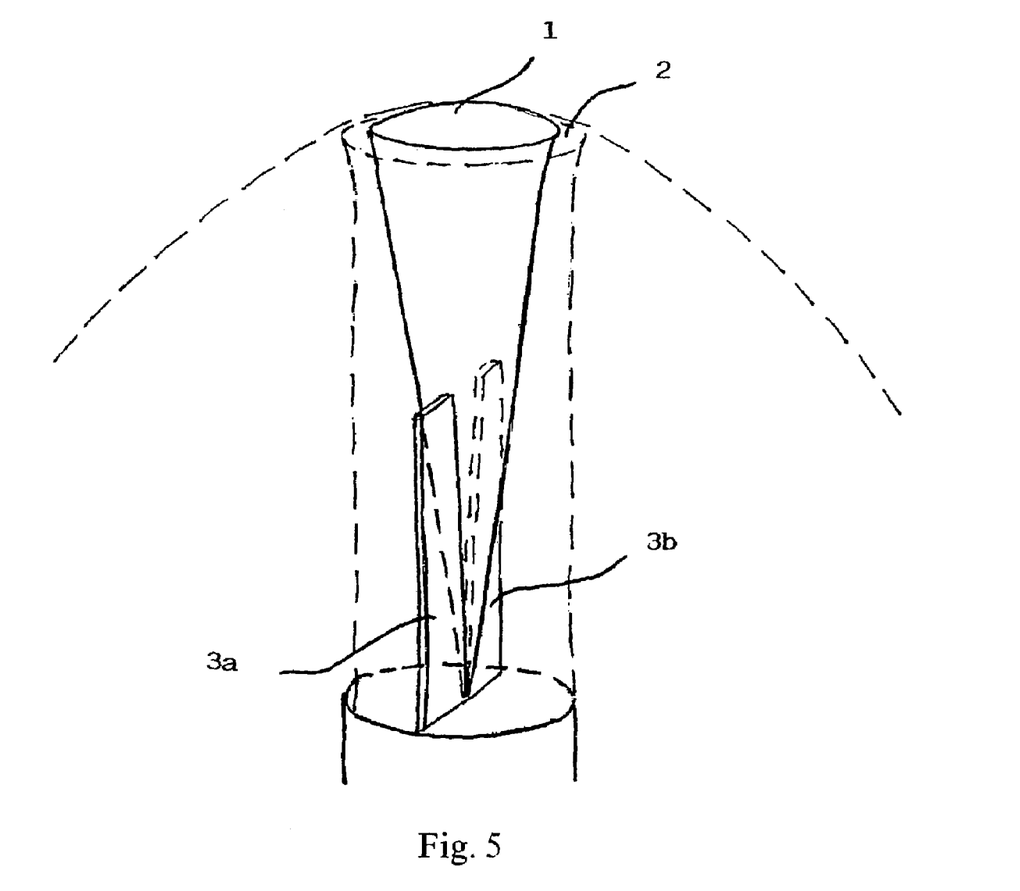

The FIG. 5 shows a transparent view of the ejection duct of a further embodiment form of the nozzle according to the present invention, wherein the two baffles (3a) and (3b) are present only at the lower portion of the ejection duct and they do not reach the opening (2).

Figure 6:
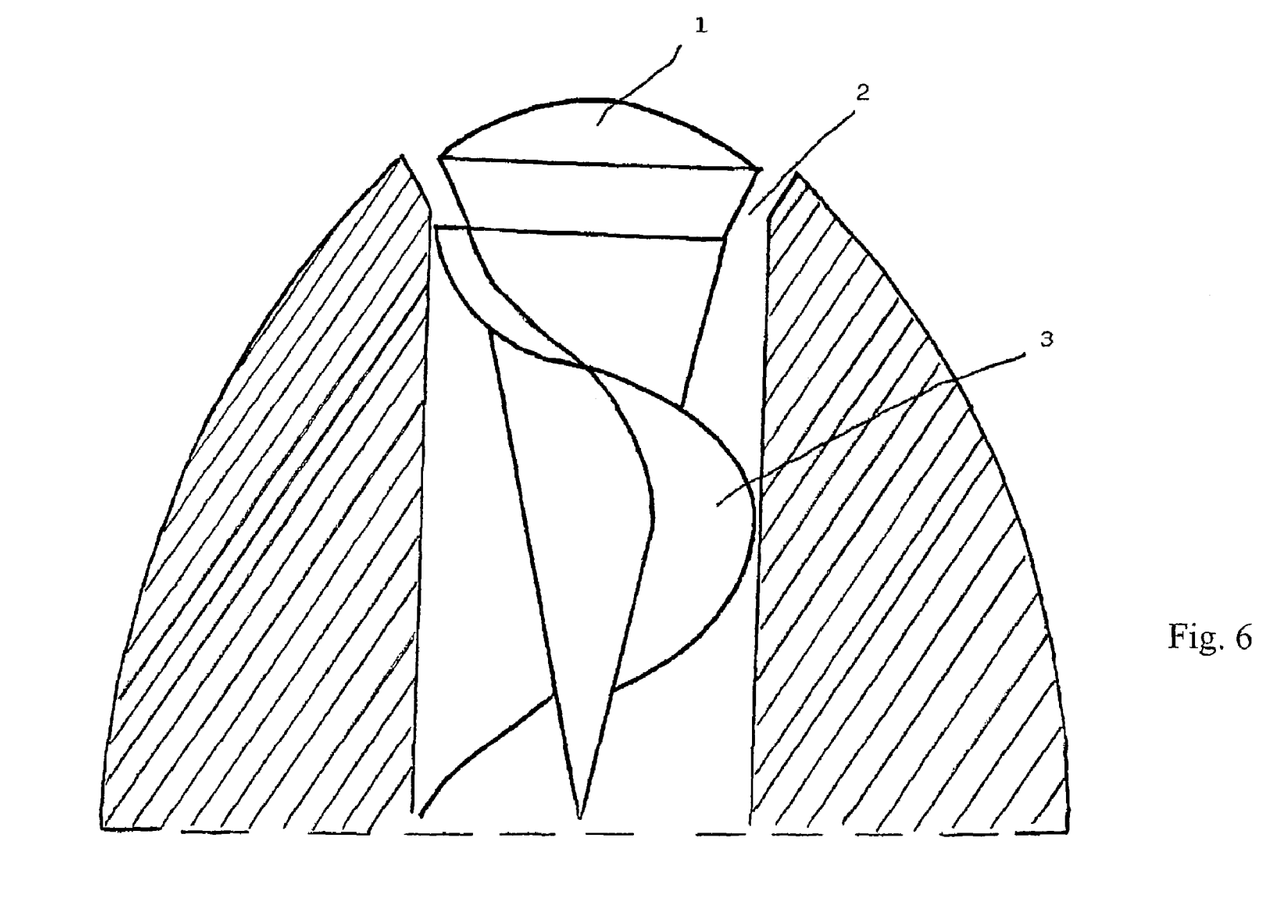

The FIG. 6 shows the ejection duct of a further embodiment form of the nozzle wherein the baffle (3) is spiral shaped wrapped around the external mantle of the central body (1) nearly along its whole height.

Figure 7:
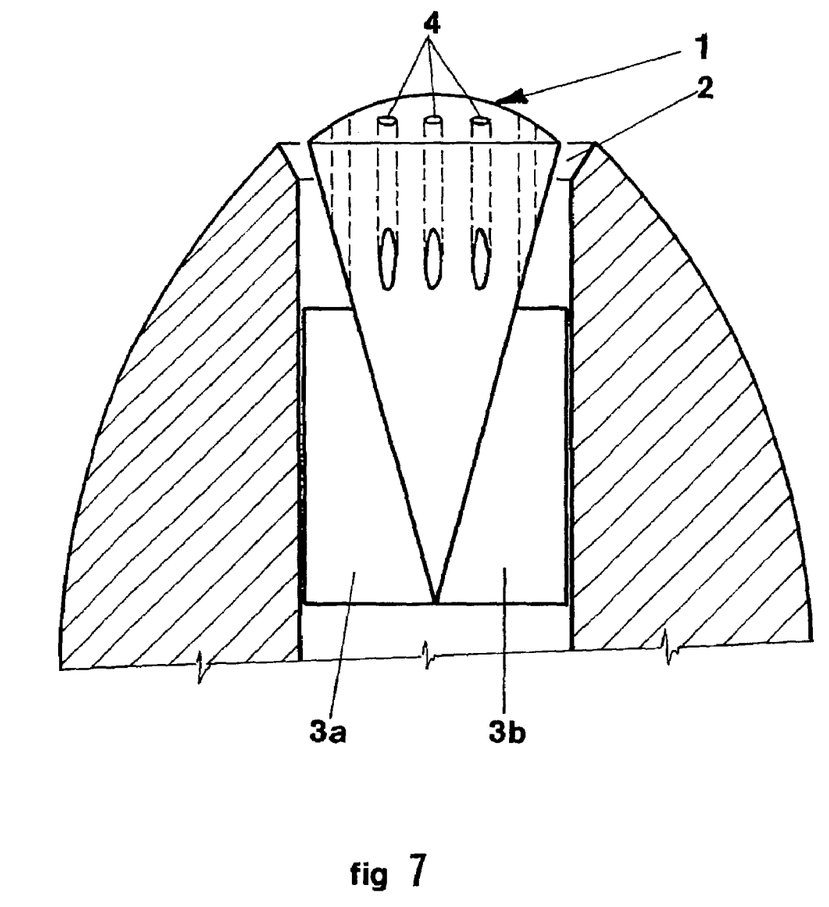
FIG. 7 shows the central body (1) comprising some ejection ducts (4) of longitudinal form.
Figure 8:
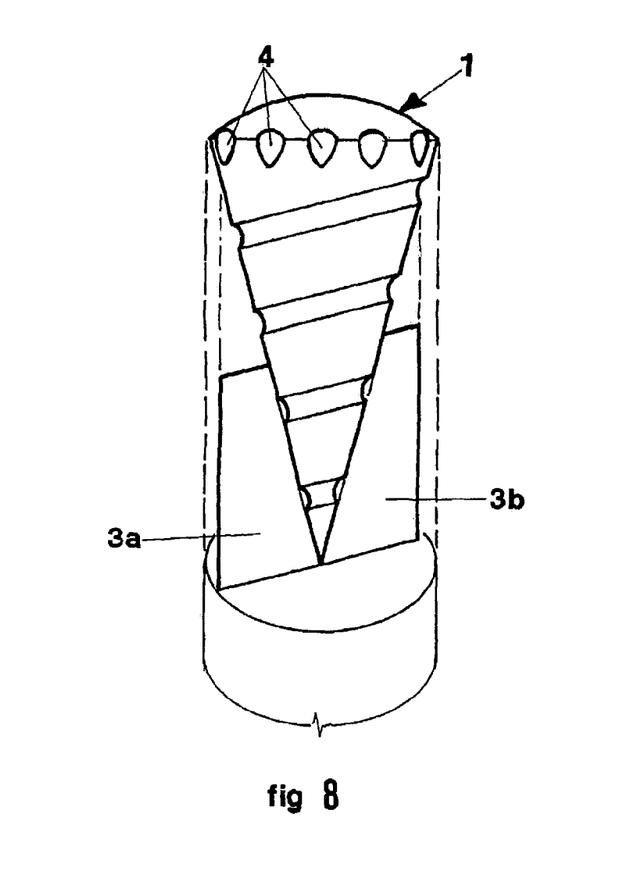
FIG. 8 shows the ejection ducts (4) having a spiral form.
Figure 9:
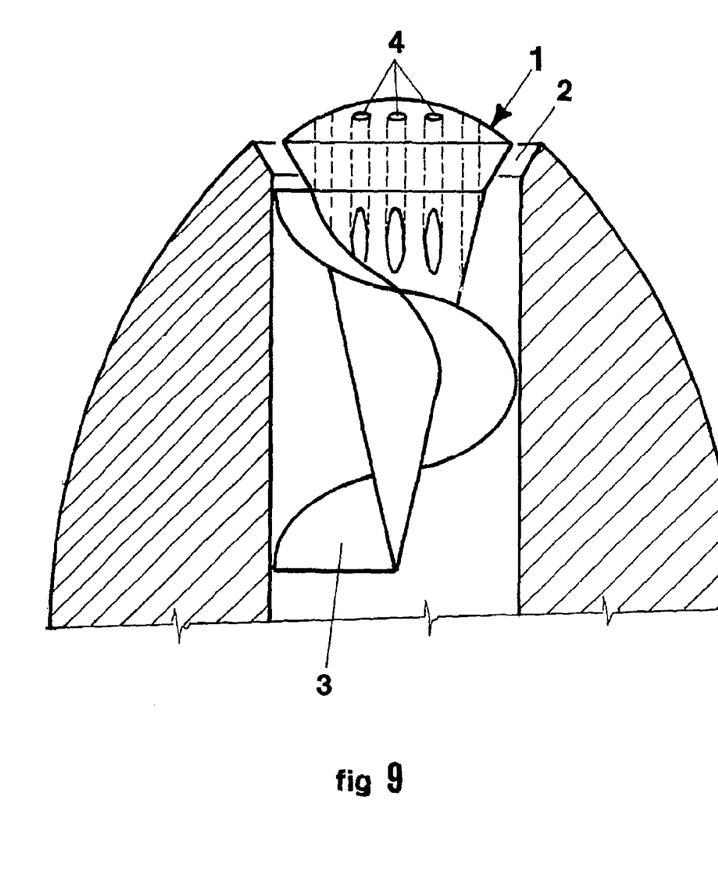
FIG. 9 is similar to FIG. 6, but the central body (1) comprises some ejection ducts (4).

The FIGS. 7 to 9 show the central body (1) comprising some ejection ducts (4). This kind of embodiment is particularly suitable for the washing of the cavities as the spiral baffle generates in the washing solution a vortical rotatory motion allowing to remove more easily the secretions adherent to the mucosa of the cavities.

Without leaving the field of the invention the spiral baffle may be present only at the upper portion or at the lower portion of the ejection duct or it may be free to spin around the central body (1).

The central body (1) may have one or more holes, or additional openings having various shapes, for example zigzag, in order to allow also the spraying of the central zone of the interested cavity.

Without leaving the field of the invention, it is possible for one skilled in the art to make all the changes to the nozzle of the present invention suggested by his experience and by the natural evolution of the art.

The nozzle of the invention allows to obtain a uniform distribution of lavage and/or pharmacological solutions on the whole mucosa of the cavity.

The kind of the substance sprayable by the nozzle of the present invention may be either a solution useful to the irrigation for the washing of the cavities or a pharmacological solution containing an active principle to vehiculate, such as, for example, vitamin A but also solid compounds or mixtures of suitably micronized solid compounds.

Therefore the nozzle of the present invention is useful either for the lavage of nasal, auricular, vaginal and rectal cavities, or for the administration of active principles by absorption through the relevant mucosa. Said nozzle for such a purpose may be used in a device, for example, as the one disclosed by the Patent Application WO 96/29044, on a common propeller-free spray dispenser, an aerosol or nebulizer.

The invention claimed is:

1. Nozzle for the lavage or for the administration of active principles into nasal, auricular, vaginal and rectal cavities, comprising a cylindrical ejection duct coaxial with the nozzle, at least one substantially annular slot opening (2), a cone shaped central body (1) coaxial with the nozzle, having the basis at the opening (2) and the vertex directed towards the basis of the nozzle, and at least one baffle (3) connecting the central body (1) to the internal walls of the ejection duct, wherein the ejection duct and the central body present their upper ends widened towards the outside.

2. Nozzle as claimed in claim 1 having an elliptical cross section.

3. Nozzle as claimed in claim 1 wherein said ejection duct has an elliptical cross section.

4. Nozzle as claimed in claim 3 wherein the opening (2) has an elliptical shape.

5. Nozzle as claimed in claim 1 wherein said ejection duct has a circular cross section.

6. Nozzle as claimed in claim 5 wherein the opening (2) has a circular shape.

7. Nozzle as claimed in claim 1 wherein said central body (1) has an elliptical cross section.

8. Nozzle as claimed in claim 1 wherein said central body (1) has a circular cross section.

9. Nozzle as claimed in claim 1 comprising two baffles (3a) and (3b).

10. Nozzle as claimed in claim 9 wherein said baffles (3a) and (3b) are aligned one with the other.

11. Nozzle as claimed in claim 9 wherein said baffles (3a) and (3b) reach as far as the height of the body.

12. Nozzle as claimed in claim 9 wherein said baffles (3a) and (3b) are present only at the lower portion of the ejection duct.

13. Nozzle as claimed in claim 9 wherein said baffles consist of two short segments at any portion of the ejection duct.

14. Nozzle as claimed in claim 9 wherein said baffles (3a) and (3b) divide the opening (2) in two openings (2a) and (2b).

15. Nozzle as claimed in claim 14 wherein said openings (2a) and (2b) have semicircular shape.

16. Nozzle as claimed in claim 14 wherein said openings (2a) and (2b) have semielliptical shape.

17. Nozzle as claimed in claim 1 wherein the baffle (3) is coiled around the central body (1).

18. Nozzle as claimed in claim 17 wherein the baffle (3) is present at the whole height of the ejection duct.

19. Nozzle as claimed in claim 17 characterized in that said baffle (3) is present only at the lower portion of the ejection duct.

20. Nozzle as claimed in claim 1, wherein said central body (1) comprises some ejection ducts (4).

21. Nozzle for the lavage or for the administration of active principles into nasal, auricular, vaginal and rectal cavities, comprising a cylindrical ejection duct coaxial with the nozzle and having an elliptical cross section, at least one opening (2) having a substantially annular slot, a cone shaped central body (1) coaxial with the nozzle, having the basis at the opening (2) and the vertex directed towards the basis of the nozzle and at least one baffle (3) connecting the central body (1) to the internal walls of the ejection duct, said ejection duct and said central body showing the upper end widened towards the outside.

22. Nozzle for the lavage or for the administration of active principles into nasal, uricular, vaginal and rectal cavities, comprising a cylindrical ejection duct coaxial with the nozzle, at least one opening (2) having a substantially annular slot, a cone shaped central body (1) coaxial with the nozzle and having an elliptical cross section, said body having the basis at the opening (2) and the vertex directed towards the basis of the nozzle and at least one baffle (3) connecting the central body (1) to the internal walls of the ejection duct, said ejection duct and said central body showing the upper end widened towards the outside.

* * * * *